(12) United States Patent
Wright et al.

(10) Patent No.: US 10,064,987 B2
(45) Date of Patent: Sep. 4, 2018

(54) PREVENTING OVER-DELIVERY OF DRUG

(75) Inventors: Nigel Wright, California, PA (US); Tom Monahan, Wexford, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 940 days.

(21) Appl. No.: 13/982,395

(22) PCT Filed: Jan. 26, 2012

(86) PCT No.: PCT/US2012/022674
§ 371 (c)(1),
(2), (4) Date: Oct. 15, 2013

(87) PCT Pub. No.: WO2012/106174
PCT Pub. Date: Aug. 9, 2012

(65) Prior Publication Data
US 2014/0039447 A1    Feb. 6, 2014

Related U.S. Application Data

(60) Provisional application No. 61/437,966, filed on Jan. 31, 2011.

(51) Int. Cl.
*A61M 31/00* (2006.01)
*A61M 1/30* (2006.01)
(Continued)

(52) U.S. Cl.
CPC .......... *A61M 1/30* (2013.01); *A61M 5/16827* (2013.01); *A61M 5/172* (2013.01);
(Continued)

(58) Field of Classification Search
CPC .. A61M 5/14; A61M 5/14232; A61M 5/1684; A61M 5/16827; A61M 5/30;
(Continued)

(56) References Cited

U.S. PATENT DOCUMENTS 3,734,080 A    5/1973  Petterson et al.
4,775,369 A   10/1988  Schwartz
(Continued)

FOREIGN PATENT DOCUMENTS

CN    1128497    8/1996
CN    1489483    4/2004
(Continued)

OTHER PUBLICATIONS

"System and Method for RFID Usage in the Proper Administration of Medications", ip.com Journal, ip.com, Inc., West Henrietta, NY, US., Apr. 24, 2008.

*Primary Examiner* — Edelmira Bosques
*Assistant Examiner* — Tiffany Legette-Thompson
(74) *Attorney, Agent, or Firm* — Fish & Richardson P.C.

(57) ABSTRACT

This disclosure relates to preventing over-delivery of a drug and related systems and methods. The method includes receiving, from a drug delivery device, information pertaining to a desired amount of fluid to be delivered by the drug delivery device and receiving information pertaining to a delivered amount of a fluid that has been delivered by the drug delivery device. The method also includes determining that the delivered amount satisfies a predetermined threshold amount and in response to the determination, detecting whether an initial amount of fluid provided to the drug delivery device corresponds to the desired amount of fluid to be delivered.

8 Claims, 6 Drawing Sheets

(51) Int. Cl.
  *G06F 19/00* (2018.01)
  *A61M 5/168* (2006.01)
  *A61M 5/172* (2006.01)
  *A61M 1/14* (2006.01)
  *A61M 5/36* (2006.01)
  *A61M 5/142* (2006.01)

(52) U.S. Cl.
  CPC ............ *G06F 19/3468* (2013.01); *A61M 1/14* (2013.01); *A61M 5/14232* (2013.01); *A61M 5/1684* (2013.01); *A61M 5/365* (2013.01); *A61M 2205/14* (2013.01); *A61M 2205/3317* (2013.01)

(58) Field of Classification Search
  CPC ...... A61M 5/36; A61M 5/365; A61M 5/1782; A61M 5/14323; A61M 5/172; A61M 2205/3317; A61M 2205/14; A61M 1/14; A61M 1/30; G06F 19/3468; G06F 19/34; A61J 1/1406; A61J 1/20; A61J 1/2006; A61J 1/2089; G05D 7/00; G16H 80/00
  USPC ............................................ 604/500, 411, 67
  See application file for complete search history.

(56) References Cited

U.S. PATENT DOCUMENTS

| | | |
|---|---|---|
| 4,850,972 A | 7/1989 | Schulman et al. |
| 4,898,578 A | 2/1990 | Rubalcaba |
| 4,915,688 A | 4/1990 | Bischof et al. |
| 4,925,444 A | 5/1990 | Orkin et al. |
| 4,943,279 A | 7/1990 | Samiotes et al. |
| 4,946,439 A | 8/1990 | Eggers |
| 4,959,050 A | 9/1990 | Bobo |
| 4,966,579 A | 10/1990 | Polaschegg |
| 4,981,467 A | 1/1991 | Bobo et al. |
| 5,037,390 A | 8/1991 | Raines et al. |
| 5,041,086 A | 8/1991 | Koenig et al. |
| 5,047,014 A | 9/1991 | Mosebach et al. |
| 5,049,129 A | 9/1991 | Zdeb et al. |
| 5,053,019 A | 10/1991 | Duffy |
| 5,057,076 A | 10/1991 | Polaschegg |
| 5,074,756 A | 12/1991 | Davis |
| 5,078,683 A | 1/1992 | Sancoff et al. |
| 5,102,392 A | 4/1992 | Sakai et al. |
| 5,122,123 A | 6/1992 | Vaillancourt |
| 5,122,129 A | 6/1992 | Olson et al. |
| 5,127,618 A | 7/1992 | Page et al. |
| 5,169,388 A | 12/1992 | McPhee |
| 5,176,631 A | 1/1993 | Koenig |
| 5,193,990 A | 3/1993 | Kamen et al. |
| 5,207,642 A | 5/1993 | Orkin et al. |
| 5,211,201 A | 5/1993 | Kamen et al. |
| 5,213,483 A | 5/1993 | Flaherty et al. |
| 5,246,347 A | 9/1993 | Davis |
| 5,252,044 A | 10/1993 | Raines et al. |
| 5,256,157 A | 10/1993 | Samiotes et al. |
| 5,304,126 A | 4/1994 | Epstein et al. |
| 5,304,165 A | 4/1994 | Haber et al. |
| 5,317,506 A | 5/1994 | Coutre et al. |
| 5,324,258 A | 6/1994 | Rohrbough |
| 5,329,976 A | 7/1994 | Haber et al. |
| 5,378,231 A | 1/1995 | Johnson et al. |
| 5,382,232 A * | 1/1995 | Hague .................. A61M 5/365 128/DIG. 13 |
| 5,392,638 A | 2/1995 | Kawahara |
| 5,401,237 A | 3/1995 | Tachibana et al. |
| 5,421,812 A | 6/1995 | Langley et al. |
| 5,431,626 A | 7/1995 | Bryant et al. |
| 5,431,627 A | 7/1995 | Pastrone et al. |
| 5,438,510 A | 8/1995 | Bryant et al. |
| 5,445,621 A | 8/1995 | Poli et al. |
| 5,464,392 A | 11/1995 | Epstein et al. |
| 5,494,822 A | 2/1996 | Sadri |
| 5,496,273 A | 3/1996 | Pastrone et al. |
| 5,531,697 A | 7/1996 | Olsen et al. |
| 5,531,698 A | 7/1996 | Olsen |
| 5,533,389 A | 7/1996 | Kamen et al. |
| 5,547,470 A | 8/1996 | Johnson et al. |
| 5,552,118 A | 9/1996 | Mayer |
| 5,573,502 A | 11/1996 | LeCocq et al. |
| 5,575,310 A | 11/1996 | Kamen et al. |
| 5,578,223 A | 11/1996 | Bene et al. |
| 5,609,575 A | 3/1997 | Larson et al. |
| 5,616,124 A | 4/1997 | Hague et al. |
| 5,641,892 A | 6/1997 | Larkins et al. |
| 5,643,218 A | 7/1997 | Lynn et al. |
| 5,651,775 A | 7/1997 | Walker et al. |
| 5,698,090 A | 12/1997 | Bene et al. |
| 5,713,865 A | 2/1998 | Manning et al. |
| 5,743,886 A | 4/1998 | Lynn et al. |
| 5,745,378 A | 4/1998 | Barker et al. |
| 5,752,931 A | 5/1998 | Nazarian et al. |
| 5,755,563 A | 5/1998 | Clegg et al. |
| 5,785,701 A | 7/1998 | Sams et al. |
| 5,800,387 A | 9/1998 | Duffy et al. |
| 5,816,779 A | 10/1998 | Lawless et al. |
| 5,843,035 A | 12/1998 | Bowman et al. |
| 5,873,872 A | 2/1999 | Thibault et al. |
| 5,897,526 A | 4/1999 | Vaillancourt |
| 5,916,197 A | 6/1999 | Reilly et al. |
| 5,925,011 A | 7/1999 | Faict et al. |
| 5,935,099 A | 8/1999 | Peterson et al. |
| 5,935,105 A | 8/1999 | Manning et al. |
| 5,938,636 A | 8/1999 | Kramer et al. |
| 5,941,848 A | 8/1999 | Nishimoto et al. |
| 5,989,237 A | 11/1999 | Fowles et al. |
| 5,989,423 A | 11/1999 | Kamen et al. |
| 6,017,318 A | 1/2000 | Gauthier et al. |
| 6,019,750 A | 2/2000 | Fowles et al. |
| 6,041,801 A | 3/2000 | Gray et al. |
| 6,065,941 A | 5/2000 | Gray et al. |
| 6,068,612 A | 5/2000 | Bowman et al. |
| 6,070,761 A | 6/2000 | Bloom et al. |
| 6,077,246 A | 6/2000 | Kullas et al. |
| 6,099,492 A | 8/2000 | Le |
| 6,110,153 A | 8/2000 | Davis et al. |
| 6,117,103 A | 9/2000 | Tverskoy et al. |
| 6,123,686 A | 9/2000 | Olsen et al. |
| 6,126,637 A | 10/2000 | Kriesel et al. |
| 6,142,008 A | 11/2000 | Cole et al. |
| 6,210,361 B1 | 4/2001 | Kamen et al. |
| 6,210,591 B1 | 4/2001 | Krivitski |
| 6,241,704 B1 | 6/2001 | Peterson et al. |
| 6,269,340 B1 | 7/2001 | Ford et al. |
| 6,299,131 B1 | 10/2001 | Ryan |
| 6,302,653 B1 | 10/2001 | Bryant et al. |
| 6,321,941 B1 | 11/2001 | Argentieri et al. |
| 6,416,718 B1 | 7/2002 | Maiefski et al. |
| 6,464,667 B1 | 10/2002 | Kamen et al. |
| 6,468,242 B1 | 10/2002 | Wilson et al. |
| 6,471,872 B2 | 10/2002 | Kitaevich et al. |
| 6,475,180 B2 | 11/2002 | Peterson et al. |
| 6,489,896 B1 | 12/2002 | Platt et al. |
| 6,527,758 B2 | 3/2003 | Ko |
| 6,575,930 B1 | 6/2003 | Trombley et al. |
| 6,604,908 B1 | 8/2003 | Bryant et al. |
| 6,610,024 B1 | 8/2003 | Benatti |
| 6,616,633 B1 | 9/2003 | Butterfield et al. |
| 6,622,542 B2 | 9/2003 | Derek et al. |
| 6,658,396 B1 | 12/2003 | Tang et al. |
| 6,692,478 B1 | 2/2004 | Paradis |
| 6,695,803 B1 | 2/2004 | Robinson et al. |
| 6,699,230 B2 | 3/2004 | Jaafar et al. |
| 6,726,656 B2 | 4/2004 | Kamen et al. |
| 6,731,971 B2 | 5/2004 | Evans et al. |
| 6,736,972 B1 | 5/2004 | Matson |
| 6,780,322 B1 | 8/2004 | Bissler et al. |
| 6,802,892 B2 | 10/2004 | Newman et al. |
| 6,877,713 B1 | 4/2005 | Gray et al. |
| 6,953,323 B2 | 10/2005 | Childers et al. |
| 6,985,870 B2 | 1/2006 | Martucci et al. |
| 6,986,759 B1 | 1/2006 | Jeremijevic |

(56) References Cited

U.S. PATENT DOCUMENTS

| | | |
|---|---|---|
| 7,029,456 B2 | 4/2006 | Ware et al. |
| 7,060,049 B2 | 6/2006 | Trombley et al. |
| 7,074,216 B2 | 7/2006 | Fowles et al. |
| 7,092,796 B2 | 8/2006 | Vanderveen |
| 7,128,105 B2 | 10/2006 | Tribble et al. |
| 7,150,735 B2 | 12/2006 | Hickle |
| 7,204,823 B2 | 4/2007 | Estes et al. |
| 7,214,210 B2 | 5/2007 | Kamen et al. |
| 7,326,186 B2 | 2/2008 | Trombley et al. |
| 7,338,470 B2 | 3/2008 | Katz et al. |
| 7,347,849 B2 | 3/2008 | Brugger et al. |
| 7,427,281 B2 | 9/2008 | Uber |
| 7,517,332 B2 | 4/2009 | Tonelli et al. |
| 7,559,524 B2 | 7/2009 | Gray et al. |
| 7,575,567 B2 | 8/2009 | Simpkins |
| 7,628,184 B2 | 12/2009 | Py et al. |
| 7,632,078 B2 | 12/2009 | Demers et al. |
| 7,641,626 B2 | 1/2010 | Tonelli et al. |
| 7,654,976 B2 | 2/2010 | Peterson et al. |
| 7,662,139 B2 | 2/2010 | Demers et al. |
| 7,668,731 B2 | 2/2010 | Martucci et al. |
| 7,699,806 B2 | 4/2010 | Ware et al. |
| 7,762,989 B2 | 7/2010 | Simpson |
| 7,766,873 B2 | 8/2010 | Moberg et al. |
| 7,815,621 B2 | 10/2010 | Mann et al. |
| 7,837,647 B2 | 11/2010 | Estes et al. |
| 7,837,651 B2 | 11/2010 | Bishop et al. |
| 7,905,861 B2 | 3/2011 | Rhinehart et al. |
| 7,922,708 B2 | 4/2011 | Estes et al. |
| 7,967,783 B2 | 6/2011 | Rebours |
| 7,967,785 B2 | 6/2011 | Morgan et al. |
| 7,981,101 B2 | 7/2011 | Walsh |
| 7,981,280 B2 | 7/2011 | Carr et al. |
| 7,985,198 B2 | 7/2011 | Von et al. |
| 7,998,115 B2 | 8/2011 | Bedingfield |
| 2002/0045571 A1 | 4/2002 | Liu et al. |
| 2002/0127150 A1 | 9/2002 | Sasso |
| 2003/0153895 A1 | 8/2003 | Leinsing |
| 2003/0191445 A1 | 10/2003 | Wallen et al. |
| 2004/0182471 A1 | 9/2004 | Hansen |
| 2005/0085760 A1 | 4/2005 | Ware et al. |
| 2005/0145010 A1 | 7/2005 | Vanderveen et al. |
| 2005/0203329 A1 | 9/2005 | Muto et al. |
| 2005/0209563 A1 | 9/2005 | Hopping et al. |
| 2005/0230292 A1 | 10/2005 | Beden et al. |
| 2005/0246317 A1 | 11/2005 | Turner et al. |
| 2006/0025747 A1 | 2/2006 | Sullivan et al. |
| 2006/0047270 A1* | 3/2006 | Shelton ............... A61K 9/0097 604/890.1 |
| 2006/0084905 A1 | 4/2006 | Montgomery et al. |
| 2006/0089594 A1 | 4/2006 | Landau |
| 2006/0229557 A1 | 10/2006 | Fathallah et al. |
| 2007/0062605 A1 | 3/2007 | Wilson et al. |
| 2007/0156089 A1 | 7/2007 | Yu |
| 2007/0161941 A1* | 7/2007 | Ash ..................... A61M 1/16 604/6.09 |
| 2008/0098798 A1* | 5/2008 | Riley ................... A61M 5/365 73/19.03 |
| 2008/0242915 A1 | 10/2008 | Jackson et al. |
| 2008/0269678 A1* | 10/2008 | Rebours .......... A61M 5/16827 604/118 |
| 2008/0300570 A1 | 12/2008 | Fowles et al. |
| 2008/0311007 A1 | 12/2008 | Helmerson |
| 2009/0036864 A1 | 2/2009 | Moy et al. |
| 2009/0057258 A1 | 3/2009 | Tornqvist |
| 2009/0069783 A1 | 3/2009 | Ellstrom et al. |
| 2009/0105629 A1 | 4/2009 | Grant et al. |
| 2009/0157219 A1 | 6/2009 | Parker et al. |
| 2009/0182300 A1 | 7/2009 | Radmer et al. |
| 2009/0204066 A1 | 8/2009 | Radmer et al. |
| 2009/0259216 A1* | 10/2009 | Drew .................. A61N 1/3706 604/891.1 |
| 2010/0004602 A1 | 1/2010 | Nord et al. |
| 2010/0030048 A1 | 2/2010 | Heller et al. |
| 2010/0042048 A1 | 2/2010 | Christensen |
| 2010/0069817 A1* | 3/2010 | Falkvall ............. A61M 1/1656 604/6.11 |
| 2010/0084041 A1 | 4/2010 | Fehr et al. |
| 2010/0113891 A1 | 5/2010 | Barrett et al. |
| 2010/0179506 A1 | 7/2010 | Shemesh et al. |
| 2011/0004143 A1* | 1/2011 | Beiriger ............... A61M 1/342 604/6.11 |
| 2011/0004144 A1 | 1/2011 | Beiriger et al. |
| 2011/0004145 A1 | 1/2011 | Beiriger et al. |
| 2011/0004187 A1 | 1/2011 | Beiriger |
| 2011/0054397 A1 | 3/2011 | Menot et al. |
| 2011/0077614 A1 | 3/2011 | Shay |
| 2011/0094619 A1 | 4/2011 | Steel et al. |
| 2011/0118662 A1 | 5/2011 | Mhatre et al. |
| 2011/0125085 A1 | 5/2011 | McGill et al. |
| 2011/0152770 A1 | 6/2011 | DiPerna et al. |
| 2011/0160701 A1 | 6/2011 | Wyatt et al. |
| 2011/0172603 A1 | 7/2011 | Yodfat et al. |
| 2011/0190702 A1 | 8/2011 | Stumber |
| 2011/0190703 A1 | 8/2011 | Pratt et al. |
| 2012/0209171 A1 | 8/2012 | Vedrine et al. |
| 2013/0018354 A1 | 1/2013 | Sund et al. |

FOREIGN PATENT DOCUMENTS

| | | |
|---|---|---|
| CN | 101201847 A | 6/2008 |
| EP | 0146310 | 6/1985 |
| EP | 0426273 | 5/1991 |
| EP | 0532432 | 9/1991 |
| EP | 1978256 | 10/2008 |
| GB | 2098670 | 11/1982 |
| GB | 2424966 B | 3/2007 |
| JP | 6346160 A | 2/1988 |
| JP | 187740 U | 6/1989 |
| JP | H01-87740 | 6/1989 |
| JP | 04156849 A | 5/1992 |
| JP | H0672494 A | 3/1994 |
| JP | 09299446 A | 11/1997 |
| JP | 119685 | 1/1999 |
| JP | 2002544439 A | 12/2002 |
| JP | 2003049784 A | 2/2003 |
| JP | 2005160705 A | 6/2005 |
| JP | 2008178444 A | 8/2008 |
| WO | WO1996040322 A3 | 3/1997 |
| WO | WO1999010027 A1 | 3/1999 |
| WO | WO2001002853 A2 | 1/2001 |
| WO | WO2006031857 A2 | 3/2006 |
| WO | WO2007101798 A2 | 9/2007 |
| WO | WO2008008845 A2 | 1/2008 |
| WO | WO2008009288 | 1/2008 |
| WO | WO2008064046 A2 | 5/2008 |
| WO | WO2009044221 A1 | 4/2009 |
| WO | WO2010099816 A1 | 9/2010 |
| WO | WO2010100074 A3 | 12/2010 |
| WO | WO2011054693 A1 | 5/2011 |
| WO | WO2011092068 A1 | 8/2011 |

* cited by examiner

PREVENTING OVER-DELIVERY OF DRUG

TECHNICAL FIELD

This invention relates to preventing over-delivery of drug and related systems and methods.

BACKGROUND

As soon as kidney failure is diagnosed, patients are typically given medication to help control the symptoms and slow the progress of the damage to the kidneys. Patients with chronic kidney failure generally take drugs to control the balance of minerals in the body and prevent a reduction of red blood cells (anemia).

Healthy kidneys produce the hormone erythropoietin (often shortened to "EPO"), which stimulates the production of red blood cells in the bone marrow. Red blood cells play a key role in the delivery of oxygen to tissues in the body. If the body does not have enough EPO, it can lead to anemia. This often causes a drop in physical and mental performance and an increased risk for cardio-vascular diseases. To prevent anemia, chronic renal patients normally receive a synthetic version of erythropoietin (also referred to as "EPO") that, like the natural erythropoietin, stimulates the production of red blood cells.

Anemia can be managed using a variety of different drugs. For example, since iron is also needed to produce red blood cells, many dialysis patients also take iron preparations. Venofer® (iron sucrose injection, USP) is indicated in the treatment of iron deficiency anemia in patients undergoing chronic hemodialysis who are receiving supplemental EPO therapy.

SUMMARY

In one aspect of the invention, a method is performed by a data processing apparatus. The method includes receiving, from a drug delivery device, information pertaining to a desired amount of fluid to be delivered by the drug delivery device and receiving information pertaining to a delivered amount of a fluid that has been delivered by the drug delivery device. The method also includes determining that the delivered amount satisfies a predetermined threshold amount and in response to the determination, detecting whether an initial amount of fluid provided to the drug delivery device corresponds to the desired amount of fluid to be delivered.

In another aspect of the invention, a system includes a dialysis machine, a control unit including one or more processors, a medical fluid tube connected to the dialysis machine, a bubble detector, and a computer-readable medium coupled to the control unit storing instructions which, when executed by the one or more processors, cause the one or more processors to perform operations. The operations include receiving, from a drug delivery device, information pertaining to a desired amount of fluid to be delivered by the drug delivery device and receiving information pertaining to a delivered amount of a fluid that has been delivered by the drug delivery device. The operations also include determining that the delivered amount satisfies a predetermined threshold amount and in response to the determination, detecting whether an initial amount of fluid provided to the drug delivery device corresponds to the desired amount of fluid to be delivered.

Implementations can include one or more of the following features.

In certain implementations, the initial amount of fluid provided to the drug delivery device is determined by a total amount of fluid in a drug vial.

In certain implementations, detecting whether the initial amount of fluid corresponds to the desired amount of fluid includes detecting a presence of air in a drug delivery line of the drug delivery device.

In certain implementations, upon determination of the presence of air in the drug delivery line, the method includes sending a signal to a pump of the drug delivery device to increase a pumping speed of the pump.

In certain implementations, upon determination of an absence of air in the drug delivery line, the method includes sending a signal to a pump of the drug delivery line to stop pumping fluid.

In some implementations, the signal to stop pumping fluid is sent upon determination that the delivered amount of fluid satisfies the desired amount of fluid to be delivered.

In certain implementations, the method includes sending an alert to a user interface that the desired amount of fluid does not correspond to the initial amount of fluid provided.

In certain implementations, detecting the initial amount of fluid further includes detecting the presence of air for a threshold amount of time.

In certain implementations, the threshold amount is a portion of the desired amount of fluid.

Implementations can include one or more of the following advantages.

In some implementations, the methods described prevent over-delivery of drug to a patient. Preventing over-delivery of drug to a patient can prevent harmful effects to a patient. The methods can provide for an additional layer of error correction for a drug delivery system.

DETAILED DESCRIPTION

In general, the invention relates to a method for preventing over-delivery of drug through a drug delivery device and ensuring a correct dosage of drug is delivered. In some aspects of the invention, a hemodialysis system includes a hemodialysis machine having a drug delivery device including one or more pumps and drug delivery lines connected to a blood circuit. In this way, drug can be delivered to the blood circuit. A control unit controls aspects of the hemodialysis system, including executing the methods further described below. In some implementations, medications use common packaging types that can be confused. The methods provide a verification that a patient will not be exposed to an over-delivery of a medication.

Figure 1:
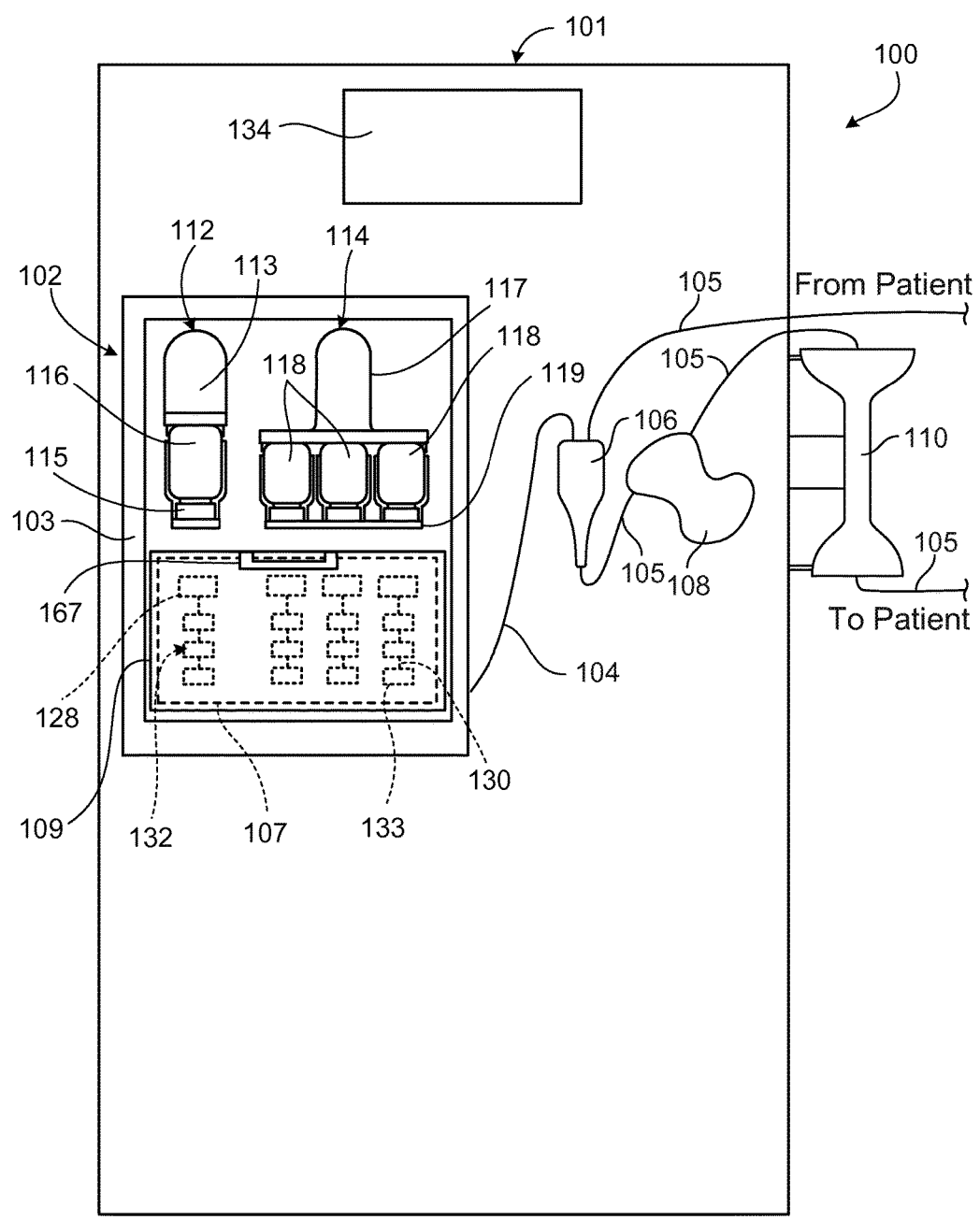
FIG. 1 is a schematic of a hemodialysis machine that includes a modular drug delivery device and a drug administration fluid line cassette secured between a door and inner face of the modular drug delivery device.

Referring to FIG. 1, a hemodialysis system 100 includes a hemodialysis machine 101 that has a drug delivery system 102. The drug delivery system 102 further includes a modular drug delivery device 103 that is attached to and exposed on the face of the hemodialysis machine 101 and a disposable drug administration fluid line set (also referred to herein as a drug administration fluid line cassette) 107 that is connected to the drug delivery device 103. A drug delivery line 104 of the drug administration fluid line cassette 107 is fluidly connected to a blood circuit of the hemodialysis system 100. The blood circuit of the hemodialysis system 100 includes, among other things, a series of blood lines 105, a drip chamber 106, and a dialyzer 110. A blood pump (e.g., a peristaltic pump) 108 is configured to pump blood through the blood circuit during treatment.

The drug delivery device 103 also includes a control unit (e.g., a microprocessor) that can control various components of the drug delivery device 103. As will be described in greater detail below, the control unit can receive signals from and send signals to the various components of the drug delivery device 103. The control unit can control the various components of the drug delivery device 103 based on information received from these components to ensure a correct amount of drug is delivered.

The hemodialysis system 100 also includes a dialysate circuit and various other components that, for the sake of simplicity, are not described in detail. During hemodialysis treatment, blood is drawn from the patient and, after passing through the drip chamber 106, is pumped through the dialyzer 110 where toxins are removed from the blood and collected in dialysate passing through the dialyzer. The cleansed blood is then returned to the patient, and the dialysate including the toxins (referred to as "spent dialysate") is disposed of or recycled and reused. As discussed in greater detail below, during the hemodialysis treatment, drugs (e.g., Epogen® and Venofer®) are also delivered to the drip chamber 106 using the drug delivery system 102. The drugs mix with the patient's blood within the drip chamber 106 and are then delivered to the patient along with the patient's blood.

Figure 3:
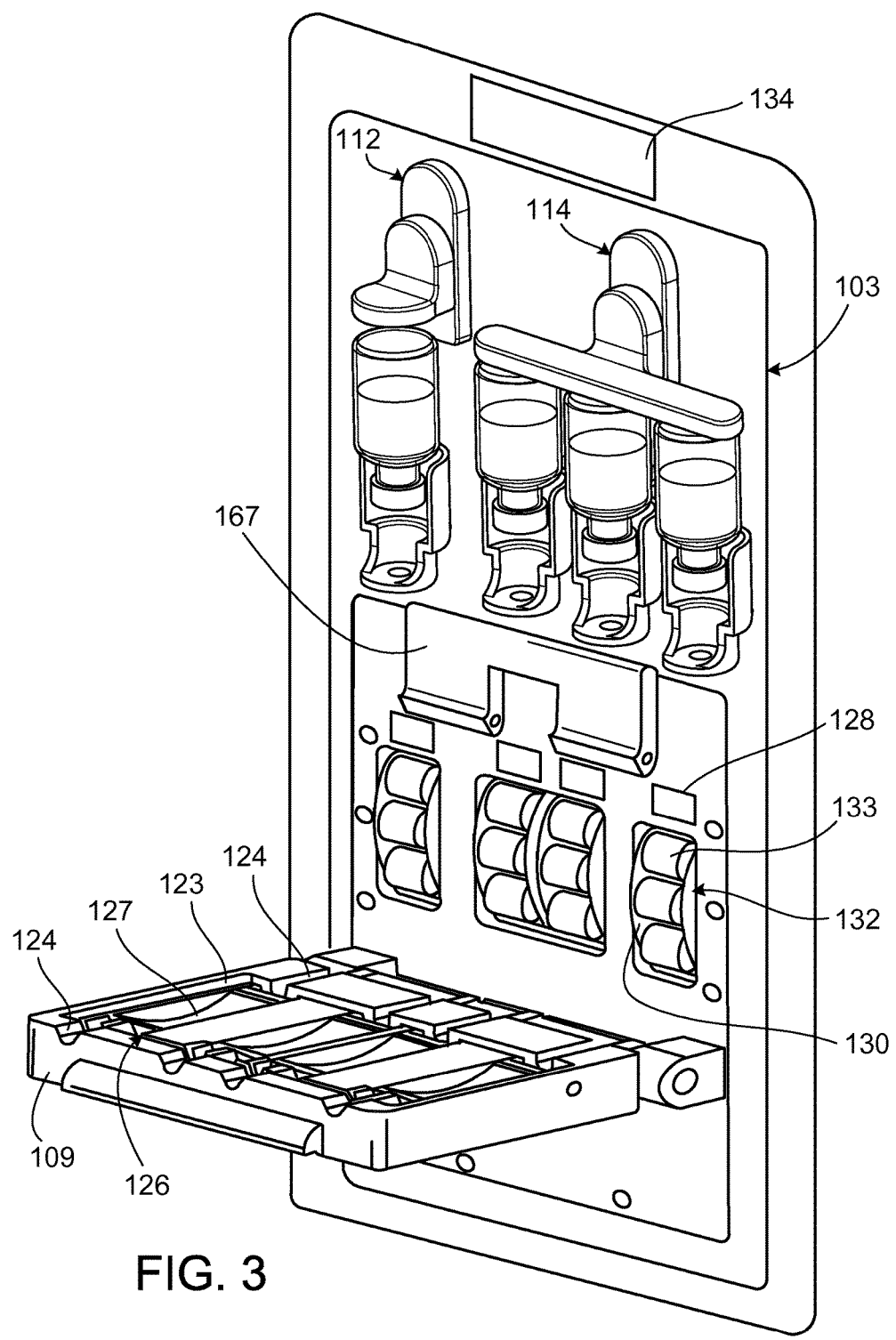
FIG. 3 is a perspective view of the hemodialysis machine of FIG. 1 with the door of the drug delivery device opened.

As shown in FIG. 3, the modular drug delivery device 103 includes a drug vial holder 112 configured to hold a single drug vial 116. Another drug vial holder 114 is configured to hold up to three drug vials 118. In the illustrated implementation, the vial 116 furthest to the left contains Venofer® and the three vials 118 to the right of the Venofer® vial 116 contain Epogen®. Venofer® (iron sucrose injection, USP) is a sterile, aqueous complex of polynuclear iron (III)-hydroxide in sucrose that is manufactured by American Regent, Inc. Venofer® is indicated in the treatment of iron deficiency anemia in patients undergoing chronic hemodialysis who are receiving supplemental erythropoietin therapy. Epogen® is a drug that stimulates the production of red blood cells and is also commonly used in dialysis patients. Epogen® is manufactured by Amgen, Inc.

The drug vial holder 112 includes a top member 113 and a bottom member 115 that can retain the single Venofer® vial 116 therebetween. The bottom member 115 has a top surface on which the cap of the inverted Venofer® vial 116 can rest. In certain implementations, the bottom member 115 includes a recess that is sized and shaped to receive a cap (or a portion of the cap) of the vial 116. This recess can help to ensure that the vial 116 is properly positioned in the vial holder 112. The bottom member 115 of the drug vial holder 112 also defines a through opening that allows an associated spike 120 of the drug administration fluid line cassette 107 to pass through the bottom member 113 and pierce a rubber seal of the Venofer® vial 116 during use.

The top and bottom members 113, 115 of the drug vial holder 112 are moveable relative to one another such that a drug vial can be compressed therebetween. In addition, the drug vial holder 112 as a whole is moveable in the vertical direction relative to the inner face of the drug delivery device 103 and relative to an associated spike 120 of the drug administration fluid line cassette 107 when the cassette 107 is disposed in the cassette compartment of the drug delivery device 103. As a result, when the cassette 107 is disposed in the cassette compartment, the top and bottom members 113, 115 of the drug vial holder 112 can be moved in unison along with the Venofer® vial 116 to cause the associated spike 120 of the cassette 107 to pierce the rubber seal of the vial 116.

The drug vial holder 114, which holds the Epogen® vials 118 during use, is similar to the drug vial holder 112 described above. In particular, this drug vial holder 114 also includes top and bottom members 117, 119 between which three Epogen® vials 118 can be held, and the bottom member 119 defines three openings through which spikes 120 of the cassette 107 can pass to pierce rubber seals of the vials 118. In some implementations, the upper surface of the bottom member 119 defines recesses that receive the caps of the Epogen® vials 118 and help to ensure that the vials 118 are properly positioned in the vial holder 114. These recesses can, for example, help to ensure that the vials 118 are aligned with the openings in the bottom member 119 to allow the spikes 120 of the cassette 107 to pierce the rubber seals of the vials 118.

Figure 2:
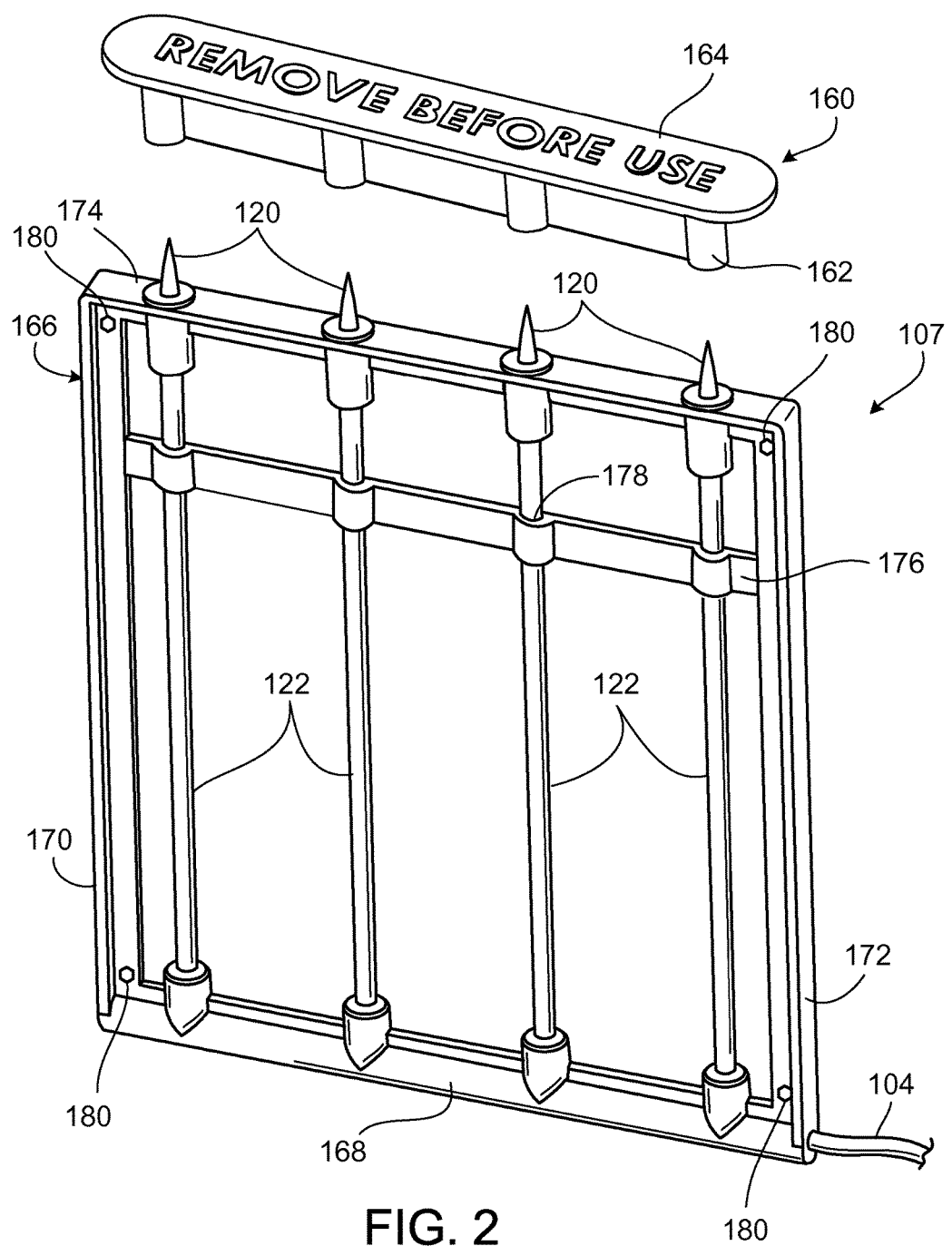
FIG. 2 is a perspective, exploded view of the drug administration fluid line cassette that is partially illustrated in FIG. 1 and a spike cover that is disposed over spikes of the drug administration fluid line cassette prior to use.

FIG. 2 illustrates the drug administration fluid line cassette 107 with a protective spike cover 160 removed from the spikes 120. As shown, feeder lines 122 are retained in a spaced apart configuration by a frame 166 of the cassette 107. The frame 166 includes along its bottom edge a manifold 168 that connect the feeder lines 122 to the drug delivery line 104, two side support members 170, 172 that extend from the manifold 168, and a top support member 174 that extends between the two side support members 170, 172. The side support members 170, 172 are attached (e.g., thermally bonded, adhesively bonded, or mechanically attached) at their bottom and top ends to the manifold 168 and top support member 174, respectively. The feeder lines 122 similarly extend between and are attached (e.g., thermally bonded, adhesively bonded, or mechanically attached) to the manifold 168 and top support member 174.

In addition to the frame 166, the cassette 107 includes a crossbar 176 that extends between the two side support members 170, 172. The crossbar 176 includes recessed regions 178 into which the feeder lines 122 are received and retained. In addition, hexagonal holes 180 are provided in the front surface of the cassette 107 (i.e., the surface of the cassette 107 that contacts the inner surface of a door 109 of the drug delivery device 103 when the cassette 107 is loaded in the cassette compartment of the drug delivery device 103). As described below, these holes 180 mate with hexagonal projections extending from the inner surface of the door 109 to secure the cassette 107 to the door 109 during use and to help ensure that only appropriate cassettes (e.g., cassettes intended for use with the drug delivery device 103 by the drug delivery device manufacturer) are used with the drug delivery device 103.

Still referring to FIG. 2, the spikes 120 are attached (e.g., thermally bonded, adhesively bonded, and/or mechanically attached) to and extend upward from the top support member 174 of the cassette 107. The drug vial spikes 120 can be formed of one or more relatively rigid medical grade plastics, such as polycarbonate or alphamethylstyrene (AMS), and the various fluid lines can be formed of a more flexible medical grade plastic, such as polyvinylchloride (PVC). Each of the spikes 120 can include, for example, a central channel that extends along the length of the spike and two openings (e.g., channels or slots) along the outer surface of the spike that lead to the central channel. The central channel of each spike is aligned with and fluidly connected to a vertical passage extending through the top support member 174.

The feeder lines 122 are in fluid communication with their associated spikes 120 via the vertical passages extending through the top support member 174. The feeder lines are also in fluid communication (via openings in the top surface of the manifold 168) with the central passage that extends through the manifold 168. The drug delivery line 104 is similarly connected to the manifold 168 and is in fluid communication with the central passage of the manifold 168. Thus, when the spikes 120 penetrate the rubber seals of the vials 116, 118 during use, drug can flow through the feeder lines 122, the manifold 168, the drug delivery line 104, and into the drip chamber 106.

The manifold 168, the side support members 170, 172, the top support member 174, and the crossbar 176 are typically formed of one or more materials that are more rigid than the material or materials from which the feeder lines 122 are made. Examples of such relatively rigid materials include polycarbonate and AMS. However, other relatively rigid materials can alternatively or additionally be used. Due to the construction and materials of the frame 166 and cross bar 176 of the cassette 107, the feeder lines 122 are held in substantially fixed positions relative to one another. As a result of this configuration, loading of the drug administration fluid line cassette 107 into the cassette compartment of the drug delivery device 103 is simplified.

Still referring to FIG. 2, the spike cover 160 is a unitary plastic structure that includes multiple tubular members 162 extending downward from an elongate structure 164. The tubular members 162 form cavities in which the drug vial spikes 120 of the cassette 107 are disposed prior to their insertion into the vials 116, 118. The cavities are sized and shaped so that the portions of the tubular members 162 forming those cavities grip their associated spikes 120 with sufficient force to prevent the cover 160 from falling off or being inadvertently knocked off the spikes 120 prior to loading the vials 116, 118 onto the spikes 120, while allowing the operator of the system to manually remove the cover 160 from the spikes 120 at the desired time. The spike cover 160 is removed from the spikes 120 of the cassette 107 prior to loading the vials 116, 118 onto the spikes 120.

Referring again to FIG. 1, which illustrates the cassette 107 in the cassette compartment of the drug delivery device 103, the spikes 120 of the cassette 107 have been inserted into the vials 116 and 118, which are retained in vial holders 112 and 114, respectively. Peristaltic pumps 132 extend from the inner face of the drug delivery device 103 and align with the feeder lines 122 (between the cross bar 176 and the manifold 168 of the cassette 107) such that when one of the pumps 132 is operated, the drug is drawn from the vial 116, 118 associated with that pump and delivered via the feeder lines 122, the manifold 168, and the drug delivery line 104 to the drip chamber 106 of the blood circuit.

Each of the feeder lines 122, as shown also in FIG. 3, passes through (e.g., is threaded through) a bubble detector 128, arranged in a spaced configuration across the inner face of the drug delivery device 103 above the peristaltic pumps 132. The bubble detectors 128 are capable of detecting air bubbles within the feeder lines 122. As a result, each of the bubble detectors 128 can determine whether its associated drug vial 116, 118 is empty during treatment, because air is drawn from the vial 116, 118 into the feeder line 122 when the vial is empty. In some implementations, the bubble detectors 128 are optical detectors. The OPB 350 bubble detector made by Optek can, for example, be used. Other types of optical detectors can alternatively or additionally be used. Similarly, other types of sensors, such as sensors utilizing ultrasound technology can be used as the bubble detectors. Examples of such sensors include the AD8/AD9 Integral Ultrasonic Air-In-Line, Air Bubble Detector and the BD8/BD9 Integral Ultrasonic Air Bubble, Air-In-Line & Liquid Level Detection Sensors (manufactured by Introtek International (Edgewood, N.Y.)). In some implementations, the bubble detector 128 includes a sensor that, in addition to sensing the presence of an air bubble within its associated feeder line 122, can sense the presence of the feeder line itself.

FIG. 3 illustrates the drug delivery device 103 with the door 109 opened and the drug administration fluid line cassette 107 removed. As shown, the inner surface of the door 109 includes a recessed region 123 that is configured to receive the rigid frame 166 of the cassette 107 and elongate slots 124 that are configured to receive the feeder lines 122 of the cassette 107 without substantially deforming the feeder lines 122. In certain implementations, the recessed region 123 and slots 124 are sized so that the frame 166 and feeder lines 122 of the cassette 107 can be snapped into the recessed region 123 and slots 124, respectively, and thus releasably secured to the door 109. The inner surface of the door 109 also includes the hexagonal projections that are configured fit into the hexagonal holes 180 formed in the cassette 107 when the cassette 107 is loaded into the door 109. The hexagonal projections can be sized and shaped to create a snap fit or a snug press fit that secures the drug administration fluid line cassette 107 to the door 109.

In addition, the inner surface of the door 109 includes spring-loaded members 126 that define recesses or raceways 127 that receive roller members of the peristaltic pumps 132 of the drug delivery device 103 when the door 109 is closed. Springs are connected to top and bottom regions of each member 126 and to an internal fixed member in the door 109 to allow the members 126 to flex in response to contact with the rollers of the peristaltic pumps 132 or in response to contact with the feeder lines 122 positioned between the members 126 and the rollers of the peristaltic pumps 132.

Still referring to FIG. 3, the peristaltic pumps 132 are positioned in a spaced configuration across the face of the drug delivery device 103. Each pump 132 includes multiple rollers 133 that compress the associated feeder line 122 in a manner to create a "pillow" of fluid (i.e., a "pillow" of air or liquid) that is pinched between two points of the feeder line 122 that are compressed by the pump rollers 133. The rollers 133 are arranged around a circumference of a rotatable frame. As the frame is rotated, the rollers 133 force the "pillow" of fluid through the feeder line 122 to the drug delivery line 104. The peristaltic pumps 132 are configured to rotate about an axis that extends in a direction that is substantially parallel to the face of the drug delivery device 103. When the cassette 107 is positioned in the cassette compartment between the inner face of the drug delivery device 103 and the closed door 109, the feeder lines 122 align with the pumps 132 and are thus pressed into the raceways 127 of the spring-loaded members 126 in the door

109. The spring force provided by the springs of the spring-loaded members 126 helps to take up tolerance between the raceways 127 and the rollers 133, and thus helps to ensure that a fixed compression force is applied to the feeder lines positioned between the raceways 127 and the rollers 133.

During operation of the pump 132, the rollers 133 are rotated from top to bottom (in the view shown in FIG. 3) and thus force pillows of fluid downward through the associated feeder line 122. When the pump 132 is being operated, vacuum pressure is applied to the drug vial 116, 118 that is connected to the feeder line 122. In certain cases, the initial pressure in the drug vial 116, 118 is equal to the ambient pressure, and when all of the drug has been delivered, the ending pressure within the vial is about −10 psi. In other words, the pressure within the drug vial 116, 118 progresses from ambient to −10 psi as the drug is delivered. The pump 132 is configured to generate a vacuum pressure within the feeder line 122 that exceeds the competing vacuum within the drug vial 116, 118. As a result, the drug is drawn from the vial 116, 118, through the drug vial spike 120 and into the feeder line 122.

The spacing of the rollers 133 about the circumference of the rotatable frames 130 of the peristaltic pumps 132 is selected so that at least one of the rollers 133 is positioned in the raceway 127 of the associated spring-loaded member 126 when the door 109 of the drug delivery device 103 is closed. This helps to ensure that the feeder lines 122 positioned between the pumps 132 and the raceways 127 are always occluded in at least one location and thus helps to prevent the drugs from passing through the feeder lines 122 to the manifold 168 when the pumps 132 are not in operation.

Referring again to FIGS. 1-3, the drug vial holders 112, 114 of the drug delivery device 103 can be equipped with various types of sensors for sensing the presence of a vial, identifying the type drug vial installed, detecting the size of the drug vials, and/or detecting the mass of the drug vials. In some implementations, each drug vial holder 112, 114 includes a sensor to sense the presence of a vial or drug container. In certain implementations, each drug vial holder 112, 114 includes a system which identifies the drug vial installed. The drug vial identification system can, for example, include a bar code reader that reads bar codes on the vials. Different types of sensors can alternatively or additionally be used. In some implementations, for example, the vial identification system uses RFID technology. Other examples of suitable sensors include color sensors for sensing the color of color-coded drug vials and/or for sensing the color of the drug within the vial, photo sensors (e.g., cameras) that are equipped with text recognition software to read text on the drug vial, capacitive sensors that permit different size vials to be detected, load cells or scales that detect the mass of the vial, and conductivity or electrical impedance sensors that can be used to determine the type of drug within the vial.

The sensors can communicate with the control unit, sending detected information to the control unit and receiving commands from the control unit. As will be described further below, the control unit can receive information and send commands to prevent the over-delivery of a drug. The control unit can also control the pumps 132 to ensure that only one of the pumps 132 is in operation at a time. This helps to ensure that drug is pulled from only one of the vials 116, 118 at a time during treatment. Upon determining that the prescribed volume of the drug has been delivered (based on monitoring the operation of the pumps 132), the control unit can turn off the pump 132 associated with that drug vial 116, 118 and turn on the pump 132 associated with the drug vial 116, 118 containing the next drug to be delivered. In addition, after the full contents of a vial have been evacuated, air will be sucked into the feeder line 122 associated with that vial and will be detected by the bubble detector 128. In response, the control unit can turn off the pump 132 associated with the empty vial and turn on the pump 132 associated with the vial containing the next drug to be delivered.

The control unit can also control certain components of the drug delivery device 103 based on signals received from the drug vial ID sensors, which indicate the presence of a vial and/or the identity of the vial contents. Such an arrangement can help to ensure that the correct vials (e.g., the correct number of vials and the vials containing the correct contents) are used for the treatment. Upon receiving signals from the drug vial ID sensors that do not match the inputted treatment information, for example, an alarm (e.g., an audible and/or visual alarm) can be activated. Alternatively or additionally, the drug delivery device 103 can be configured so that treatment cannot be initiated until the sensors detect the correct combination of vials.

The drug delivery device 103 (e.g., the control unit of the drug delivery device 103) is configured to sense if the blood pump 108 of the dialysis machine 101 is running and to pause drug delivery if the blood pump 108 is stopped. This technique prevents "pooling" of the delivered drug in the drip chamber 106 during treatment.

Still referring to FIGS. 1-3, the drug delivery device 103 further includes a user interface 134 that is connected to the control unit. The user interface 134 includes keys that allow the user to navigate through displays associated with the vials 116, 118 and set the desired dosage for each of the vials 116, 118. In addition, the user interface 134 includes start and stop keys that allow the user to start and stop the drug delivery device 103.

Any of various other types of user interfaces can alternatively or additionally be used. In some implementations, the drug delivery device includes a user interface that allows the user to select a drug to infuse from a menu. In certain implementations, the user may confirm that the drug identified by the drug vial ID sensor is correct and/or make appropriate adjustments. The user interface can be used to input and/or monitor various different treatment parameters. Examples of such parameters include drug dosage, drug delivery rate, amount of drug delivered, status of the drug delivery for each drug channel, time, percent complete, percent remaining, time remaining, time delivered, date, patient ID, patient name, alarms, alerts, etc. Such user interfaces can include a color graphical display. In certain implementations, for example, the user interface is color coded according to drug, dosing, or status of drug delivery (e.g., done, running, ready, etc.).

The hemodialysis machine 101 also includes an alarm and/or alert system to which the control unit of the hemodialysis machine 101 is connected. The alarm and/or alert system can be configured to emit a visual and/or audio alarm and/or alert. The alarm and/or alert system can further include pre-programmed alarm and/or alert limitations so that when a user modifies any aspect of the system to be outside of the limitations, or the machine itself detects any aspects of the system to be outside of the limitations, the module emits an alarm and/or alert.

Still referring to FIGS. 1-3, a method of using the hemodialysis system 100 to perform hemodialysis on a patient will now be described. Prior to beginning hemodialysis treatment on a patient, the various lines that make up the blood circuit and dialysate circuit of the hemodialysis machine are primed, and then the patient lines 105 are connected to the patient. After connecting the patient lines 105 to the patient, the blood pump 108 is activated to circulate blood through the blood circuit. A dialysate pump is also activated to pump dialysate through the dialysate circuit of the hemodialysis machine. The blood is drawn from the patient and delivered to the drip chamber 106 via the arterial patient line. The drip chamber 106 acts as an air trap such that any air in the blood is released as the blood passes through the drip chamber 106. In particular, the drip chamber 106 includes a vent through which air released from the blood can be vented from the drip chamber 106. The blood is then pumped from the drip chamber 106 to the dialyzer 110, which includes a semi-permeable membrane that divides the dialyzer 110 into two chambers. As the blood passes through one of the chambers of the dialyzer 110, dialysate from the dialysate circuit passes through the other chamber. As the blood flows by the dialysis fluid, impurities, such as urea and creatinine, diffuse through the semi-permeable membrane into the dialysate. The spent dialysate is either disposed of or recycled and reused. The cleansed blood exiting the dialyzer 110 is returned to the patient via the venous patient line.

After initiating the hemodialysis treatment, the operator of the hemodialysis system 100 (e.g., the physician, nurse, medical assistant, or patient) determines the prescribed Epogen® dose and then consults a dosing schedule for the different vial combinations that can be used to deliver the prescribed Epogen® dose. Examples of dosing schedules are described in U.S. patent application Ser. No. 12/827,119, which is herein incorporated by reference in its entirety. The operator then selects one of the Epogen® vial combinations provided based on the operator's preference and loads the selected Epogen® vials into the drug vial holders. The operator also loads a vial of Venofer® into one of the drug vial holders. In some implementations, the operator selects from various Venofer® vials that are the same size but contain different amounts of Venofer®.

The operator of the system then connects the disposable drug administration fluid line cassette 107 to the inner surface of the door 109 by inserting the frame 166 and feeder lines 122 into their corresponding recessed regions 123 and slots 124. As a result of this, the hexagonal shaped projections that extend from the inner surface of the door 109 slide into the matching holes 180 formed in the frame 166 of the drug administration fluid line cassette 107. The mating engagement of the hexagonal shaped projections and openings 180, along with the snap fit of the cassette frame 166 and feeder lines 122 into their corresponding recessed regions 123 and slots 124, helps ensure that the cassette 107 remains securely fixed to the door 109. In addition, the unique hexagonal shape of the projections and openings 180 can help to ensure that only drug administration fluid line cassettes intended for use with the drug delivery device 103 can be used. For example, drug administration fluid line cassettes that do not include holes capable of receiving the hexagonal projections of the door 109 could not be properly secured to the door 109. This would indicate to the operator that an incorrect cassette was loaded into the cassette compartment of the drug delivery device 103 and, in many cases, will prevent the door 109 from shutting and thus prevent the drug delivery device 103 from being operated with that cassette.

After loading the drug administration fluid line cassette 107 onto the door 109, the operator closes the door 109 and secures a latch 167 to hold the door 109 in the closed position. Because the cassette 107 is securely fastened to the door 109 in a desired position, the feeder lines 122 align with their associated pumps 132 and bubble detectors 128 when the door 109 is closed. Thus, as the door 109 is closed, the protruding peristaltic pumps 132 press the feeder lines 122 into the raceways 127 formed along the inner surface of the door 109, and the inner surface of the door 109 presses the feeder lines 122 into engagement with the bubble detectors 128. With the door 109 in the closed position, the spikes 120 of the cassette 107 rest directly below the holes formed in the bottom members 115, 119 of the vial holders 112, 114.

Figure 4:
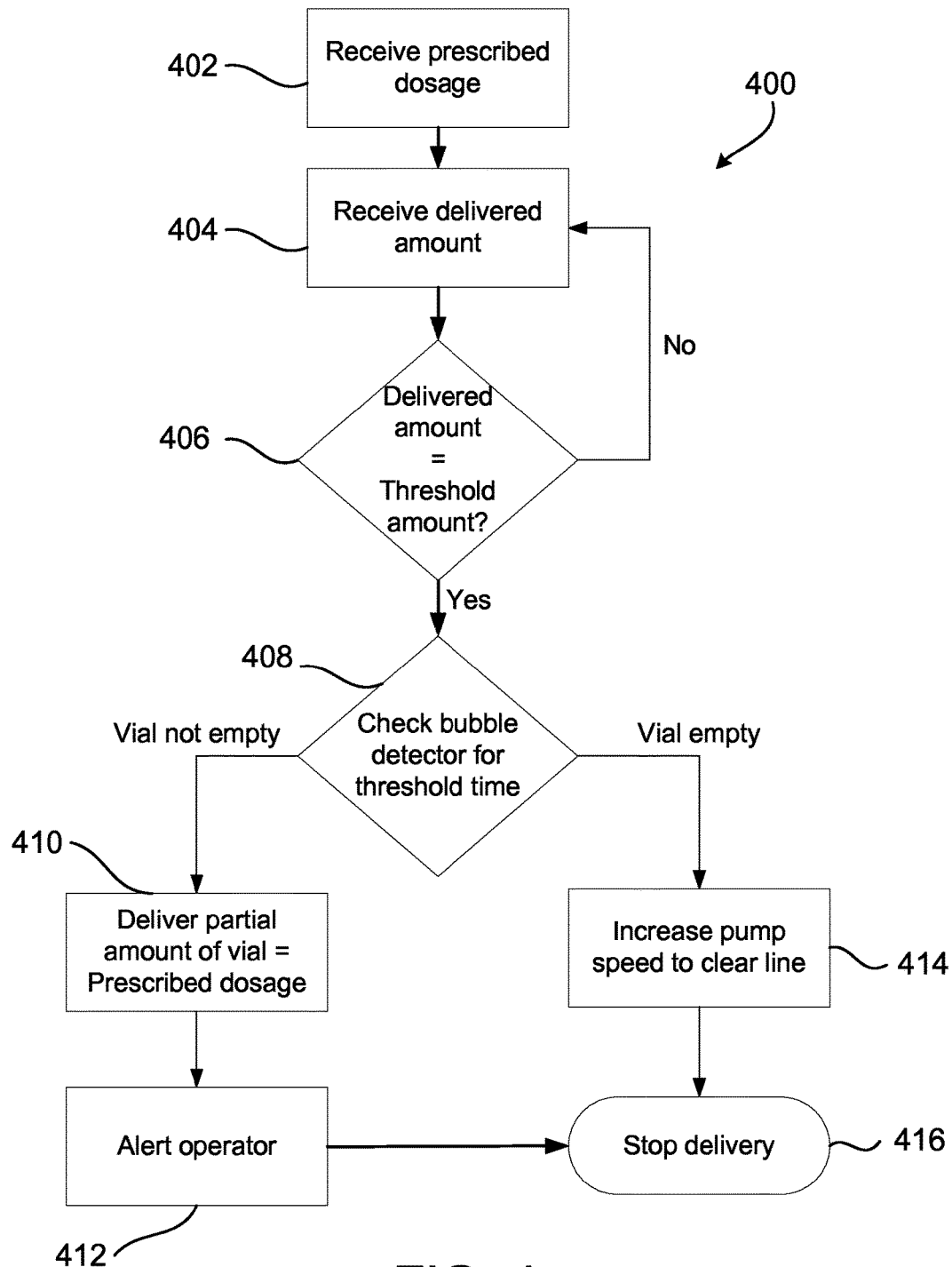
FIG. 4 is a flow chart for preventing over-delivery of a drug.

Referring also now to FIG. 4, the prescribed dosages of Venofer® and Epogen® are then entered into the drug delivery device 103 using the user interface 134 of the hemodialysis machine 101 with which the control unit of the drug delivery device 103 is in communication (402). Alternatively or additionally, the prescribed dosage of Venofer® and Epogen® can be electronically transmitted to the control unit of the drug delivery device 103 from a device, such as a portable computing device, or from a database or website accessible by the patient's prescribing physician. The operator, after reviewing the prescribed dosage entered into or transmitted to the machine, confirms that the prescribed dosage is correct by pressing a button (e.g., an "Accept" or "Confirm" button) on the user interface 134 of the hemodialysis machine 101, which initiates the spiking and priming process.

After spiking the vials 116, 118, the feeder lines 122 of the drug administration fluid line cassette 107 are primed by activating the pumps 132, either sequentially or simultaneously, which causes a portion of the drug to be drawn from each of the vials 116, 118. During the priming process, each pump 132 remains on until the drug from its associated vial 116, 118 is detected by the bubble detector 128, at which point the pump 132 is stopped and pinches off or occludes that feeder line 122. If the drug is not detected by one of the bubble detectors 128, an alarm can be activated prompting the operator to replace or adjust the drug administration fluid line cassette 107 and repeat the priming process.

After priming the feeder lines 122, Venofer® is delivered from the Venofer® vial 116 to the drip chamber 106 by activating the pump 132 associated with the Venofer® vial 116 (while leaving all of the other pumps off). The pump 132 delivers all of the Venofer® in the vial 116 unless an error is detected. Thus, the Venofer® vial 116 loaded by the operator needs to correspond to the prescribed dosage of Venofer®.

To prevent over-delivery of Venofer® in the event of an operator loading the wrong Venofer® vial, the control unit receives information from the pump 132 pertaining to how much Venofer® is being pumped from the Venofer® vial 116 (404). The control unit determines how much Venofer® is being pumped from the vial by determining the volume of fluid in each "pillow," based on the roller spacing of the peristaltic pump 132 and the inside diameter of the drug delivery line 104. By determining the amount of fluid pumped in each revolution, the control unit can determine how much Venofer® has been pumped by tracking the number of revolutions of the pump 132.

The control unit compares the amount of Venofer® pumped to a threshold amount (406). In the illustrated example, the Venofer® vials 116 contain either 50 ml or 100 ml of Venofer®. Both Venofer® vials are the same size but contain different amounts of Venofer®. The threshold amount for a 50 ml dosage is 30 ml. The control unit compares the amount pumped with the threshold amount, determining when 30 ml of Venofer® has been pumped. At this point, if the correct 50 ml Venofer® vial has been used, by including the Venofer® still in the drug delivery line 104, the vial 116 should be empty. Thus, the bubble detector 128 associated with the Venofer® feeder line 122 would start detecting air in the feeder line 122. Upon reaching the threshold amount, the control unit checks the state of the bubble detector 128 for a predetermined amount of time (408), for example, for three seconds. By checking the state of the bubble detector 128 for a predetermined amount of time, the control unit can determine whether the vial is empty or whether Venofer® is still being pumped from the vial.

If the control unit receives a signal from the bubble detector 128 that there is air in the feeder line 122 for the predetermined amount of time, the control unit sends a signal to the pump 132 to increase the pump speed to clear the lines 104, 122 (414). Increasing the speed of the pump 132 helps ensure the vial 116 is emptied and the full dosage delivered by clearing the entire attached line 122, 104.

However, if the loaded vial 116 contains the wrong amount of Venofer® and there is still Venofer® remaining in the vial 116, increasing the speed of the pump would result in over-delivery of Venofer®. In that case, upon reaching the threshold amount, the bubble detector 128 would not detect air, as there would still be Venofer® in the vial 116 and in the feeder line 122. The control unit continues to deliver until the number of revolutions would be equivalent to delivering 50 mg from the 100 mg vial, then sends a signal to the pump 132 to stop delivering Venofer®, even though the vial 116 has not been emptied. The amount of Venofer® delivered is only a portion of the vial 116, but corresponds to the prescribed dosage entered (410). In some implementations, the delivered amount corresponds to the prescribed dosage within a threshold range. The control unit alerts the operator that the loaded vial does not correspond to the entered prescribed dosage, using the alarm and/or alert system (412).

Upon determining that the prescribed dosage of Venofer® has been delivered to the drip chamber 106, the control unit causes the pump 132 associated with the Venofer® feeder line to be turned off (416).

The pump associated with the first Epogen® vial 118 (i.e., the Epogen® vial directly to the right of the Venofer® vial 116) is then activated such that Epogen® is delivered to the drip chamber 106. When the bubble detector 128 detects air in the feeder line 122, a signal is sent to the control unit, indicating that the first Epogen® vial 118 is empty. The control system then sends a signal causing the pump associated with the first Epogen® vial 118 to be turned off after assuring that an additional known volume is pumped so that the Epogen® in the line downstream of the bubble detector 128 is flushed down to a segment where the delivery of drug from the next vial can push that Epogen® remaining in the line to the drip chamber 106. In particular, the control unit ensures that the additional pumped volume is sufficient to push the Epogen® past the pump 132 and into the passage of the manifold 168 such that the next volume of drug delivered will push the Epogen® to the drip chamber 106. The control unit also sends a signal to activate the pump 132 associated with the second Epogen® vial 118 (i.e., the Epogen® vial directly to the right of the first Epogen® vial). The Epogen® delivery process described above is then repeated for the second and third Epogen® vials. The process describe above for preventing over-delivery of Venofer® can also be used for the Epogen® vials.

After delivering the desired amounts of Venofer® and Epogen® to the drip chamber 106, the drug delivery device 103 is deactivated and the drug administration fluid line cassette 107 and vials 116, 118 are removed from the drug delivery device 103 and discarded.

While the example above used 50 ml and 100 ml vials of Venofer®, any size vial can be used, with corresponding threshold amounts.

Figure 5:
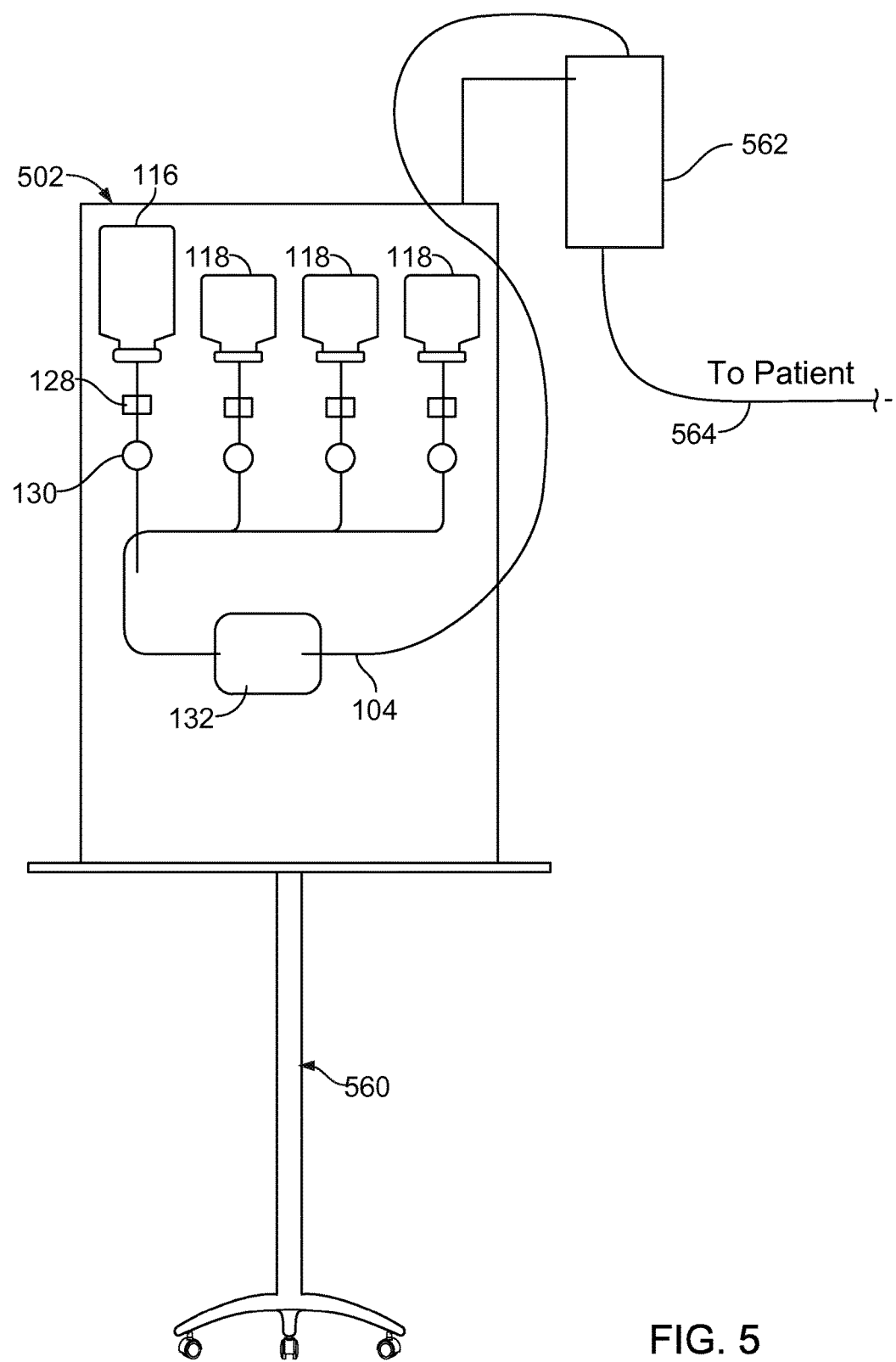
FIG. 5 is a schematic of a standalone drug delivery system.

While certain drug delivery devices described herein are provided as components of hemodialysis systems, the drug delivery devices can be used in any type of medical device that would benefit from drug infusion capabilities. Alternatively, the drug delivery devices described herein can be configured to be operated as standalone machines (i.e., not connected to another medical device). FIG. 5 illustrates a standalone drug delivery device 502, which is substantially the same as the drug delivery device 103 described above but sits on a wheeled cart 560. The drug delivery line 104 of this standalone drug delivery device 502 is connected to a drip chamber. During use, the drug(s) is/are delivered from the vials 116, 118 to the drip chamber 562. The drug(s) is/are then delivered from the drip chamber 562 to the patient via a fluid line 564. The drip chamber 562, similar to the above-described drip chamber 106, helps to ensure that any air pulled into the system from the vials does not reach the patient. The drug delivery device 502 can be used in a manner similar to the drug delivery device 103 described above to deliver drugs to a patient.

Figure 6:
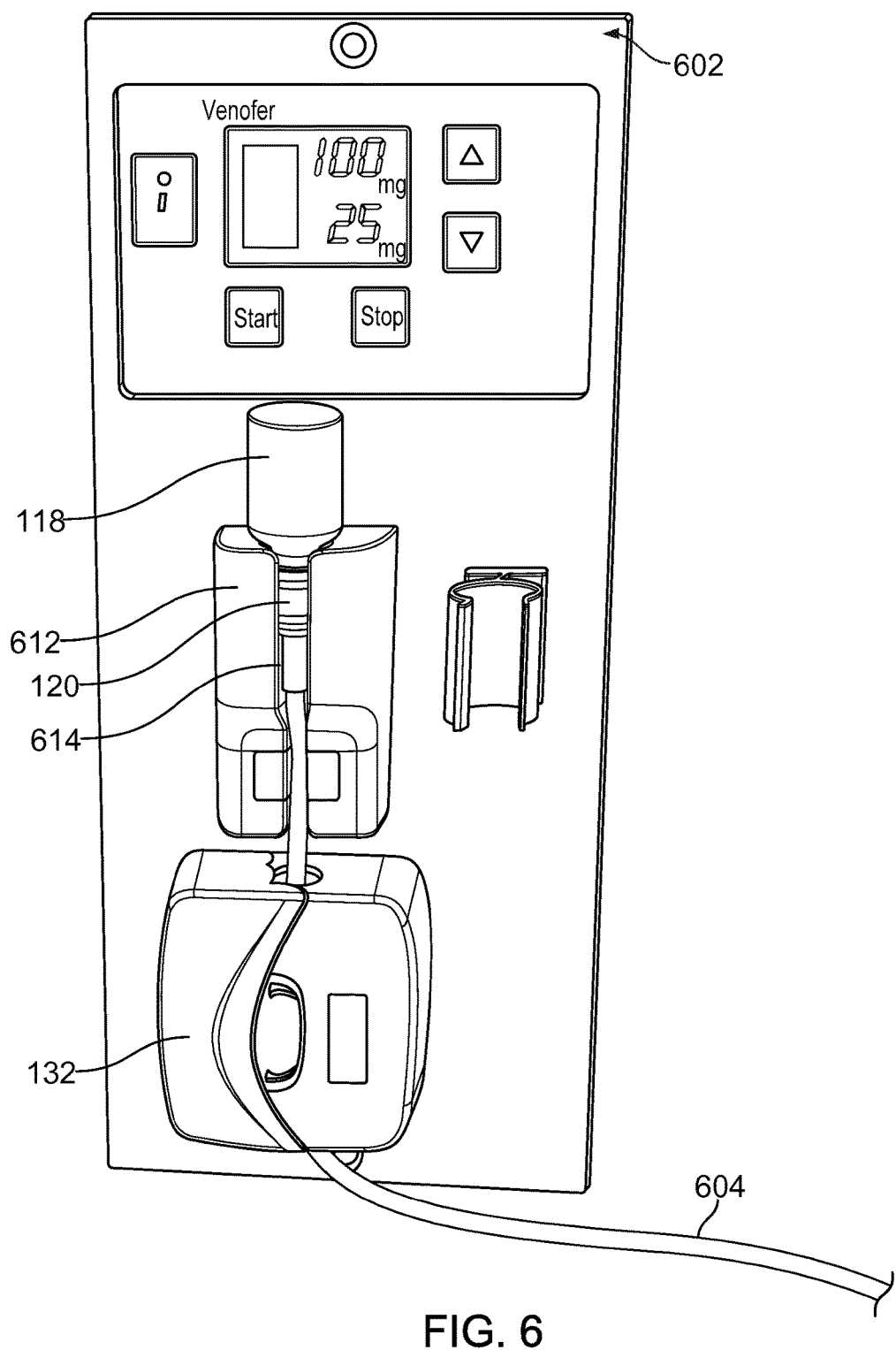
FIG. 6 is a perspective view of a modular drug delivery device that is configured for use with a single drug vial.

FIG. 6 illustrates a modular drug delivery device 602 configured to retain only a single vial detached from the hemodialysis machine. The drug delivery device 602 is substantially the same as the drug delivery device 103 described above. However, the drug delivery device 602 illustrated in FIG. 6 includes a drug vial holder that includes only one channel 614 instead of four. In addition, the drug administration fluid line set 107 that is used with the drug delivery device 602 includes a single drug delivery line 604 that is connected to the vial 118 via the drug vial spike 120. The drug delivery device 602 can be used where only one drug (e.g., Epogen®) is being administered to the patient and the prescribed dosage of that drug can be achieved with a single vial.

While drug delivery devices have been described above as including their own control unit, the drug delivery device can alternatively or additionally be configured to communicate with a control unit of the hemodialysis machine. In certain implementations, for example, the various components of the dialysis machine, including the drug delivery device components, are controlled by a single control unit of the hemodialysis machine.

While the methods of operating the drug delivery devices described above involve the user inputting a desired dosage prescription into the drug delivery device (e.g., typing the prescription into the touch screen of the drug delivery device), the prescription can alternatively be transmitted to the drug delivery device electronically. In certain implementations, for example, the desired prescription can be determined by a physician of the patient to be treated and the physician can input the prescription into a secured database or website. The prescription can then be automatically transmitted from the database to the control unit of the drug delivery device (e.g., to the control unit of the dialysis machine of which the drug delivery device is a part). This technique can help to prevent prescription input errors by the operator of the drug delivery device.

While drug vials have been described as being used in the drug delivery systems and methods described above, in certain implementations, other types of drug containers, such as bags, bottles, etc., are used.

While the drug delivery devices above have been described as being used to deliver Venofer® and/or Epogen®, it should be understood that the term "drug" as used herein incorporates pharmaceuticals as well as other fluids delivered to a patient intravenously. Other drugs that are contemplated to be automatically delivered to the patient in accordance with the various implementations of the invention include but are not limited to, phosphate binders, vitamin D, and anticoagulants.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, for example, a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of nonvolatile memory, media and memory devices, including by way of example semiconductor memory devices, for example, EPROM, EEPROM, and flash memory devices; magnetic disks, for example, internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, for example, a CRT (cathode ray tube) or LCD (liquid crystal display) monitor, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

While this specification contains many specific implementation details, these should not be construed as limitations on the scope of any disclosures or of what may be claimed, but rather as descriptions of features specific to particular implementations of particular disclosures. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method performed by a data processing apparatus, the method comprising:
   receiving at the data processing apparatus, from a drug delivery device that is part of a dialysis machine, information pertaining to a desired amount of fluid to be delivered by the drug delivery device;
   receiving at the data processing apparatus, from a pump, information pertaining to an amount of a fluid that has been delivered by the drug delivery device from a drug vial having an initial amount of fluid provided to the drug delivery device;
   determining that the amount delivered by the pump has reached a predetermined threshold amount, the threshold amount being less than the desired amount;
   in response to the determination that the threshold amount has been delivered, detecting, by a signal from a bubble detector, a presence or absence of air in a drug delivery line of the drug delivery device indicating whether delivery of the threshold amount has emptied the drug vial, and thereby determining whether the initial amount of fluid in the drug vial approximately equals the desired amount of fluid; and
   upon determination of the presence of air in the drug delivery line, automatically sending a signal to the pump via a control unit of the drug delivery device to increase a pumping speed of the pump, and upon determination of the absence of air in the drug delivery line, automatically sending a signal to the pump via the control unit to stop pumping fluid, wherein the signal to stop pumping fluid indicates a determination that the delivered amount of fluid satisfies the desired amount of fluid to be delivered.

2. The method of claim 1, further comprising:
   sending an alert to a user interface that the desired amount of fluid does not approximately equal the initial amount of fluid provided.

3. The method of claim 1, wherein detecting the initial amount of fluid further comprises detecting the presence of air for a threshold amount of time.

4. The method of claim 1, wherein the threshold amount is a portion of the initial amount of fluid.

5. A dialysis system comprising:
   a dialysis machine;
   a control unit comprising one or more processors;
   a drug delivery line connected to the dialysis machine;
   a bubble detector; and
   a computer-readable medium coupled to the control unit having instructions stored thereon which, when executed by the one or more processors, cause the one or more processors to perform operations comprising:
      receiving, from a drug delivery device that is part of the dialysis machine, information pertaining to a desired amount of fluid to be delivered by the drug delivery device;
      receiving, from a pump, information pertaining to an amount of a fluid that has been delivered by the drug delivery device from a drug vial having an initial amount of fluid provided to the drug delivery device;
      determining that the amount delivered by the pump has reached a predetermined threshold amount, the threshold amount being less than the desired amount;
      in response to the determination that the threshold amount has been delivered, detecting, by a signal from the bubble detector, a presence or absence of air in the drug delivery line of the drug delivery device indicating whether delivery of the threshold amount has emptied the drug vial, and thereby determining whether the initial amount of fluid in the drug vial approximately equals the desired amount of fluid; and
      upon determination of the presence of air in the drug delivery line, automatically sending a signal to the pump via a control unit of the drug delivery device to increase a pumping speed of the pump, and upon determination of the absence of air in the drug delivery line, automatically sending a signal to the pump via the control unit to stop pumping fluid, wherein the signal to stop pumping fluid indicates a determination that the delivered amount of fluid satisfies the desired amount of fluid to be delivered.

6. The system of claim 5, further comprising:
   sending an alert to a user interface that the desired amount of fluid does not approximately equal the initial amount of fluid provided.

7. The system of claim 5, wherein detecting the initial amount of fluid further comprises detecting the presence of air for a threshold amount of time.

8. The system of claim 5, wherein the threshold amount is a portion of the initial amount of fluid.

* * * * *